US008216817B2

(12) United States Patent
Gill et al.

(10) Patent No.: US 8,216,817 B2
(45) Date of Patent: Jul. 10, 2012

(54) PROCESS OF PRODUCING A FERMENTATION PRODUCT

(75) Inventors: George E. Gill, Raleigh, NC (US); Billie Jean Savage, Wake Forest, NC (US); Swapnil Bhargava, Thousand Oaks, CA (US)

(73) Assignee: Novozymes North America, Inc., Franklin, NC (US)

( * ) Notice: Subject to any disclaimer, the term of this patent is extended or adjusted under 35 U.S.C. 154(b) by 1161 days.

(21) Appl. No.: 12/065,939

(22) PCT Filed: Sep. 19, 2006

(86) PCT No.: PCT/US2006/036474
§ 371 (c)(1),
(2), (4) Date: Mar. 6, 2008

(87) PCT Pub. No.: WO2007/035730
PCT Pub. Date: Mar. 29, 2007

(65) Prior Publication Data
US 2008/0268512 A1    Oct. 30, 2008

Related U.S. Application Data

(60) Provisional application No. 60/718,849, filed on Sep. 20, 2005.

(51) Int. Cl.
*C12P 7/10* (2006.01)
*C12P 7/08* (2006.01)
*C12N 9/34* (2006.01)
*C12N 9/36* (2006.01)

(52) U.S. Cl. ......... 435/165; 435/163; 435/204; 435/205

(58) Field of Classification Search ............... 435/162
See application file for complete search history.

(56) References Cited

U.S. PATENT DOCUMENTS

| 4,316,956 | A | 2/1982 | Lutzen |
| 5,231,017 | A | 7/1993 | Lantero et al. |
| 5,879,509 | A * | 3/1999 | Sharyo et al. ................... 162/5 |
| 6,187,576 | B1 * | 2/2001 | Svendsen et al. ............ 435/202 |
| 2002/0006647 | A1 * | 1/2002 | Veit et al. .................... 435/162 |

(Continued)

FOREIGN PATENT DOCUMENTS

CA    1143677    3/1983
(Continued)

OTHER PUBLICATIONS

Montesinos et al., Enzyme and Microbial Technology, vol. 27, pp. 362-370 (2000).

*Primary Examiner* — Chris R Tate
*Assistant Examiner* — Douglas F White
(74) *Attorney, Agent, or Firm* — Elias Lambiris (57) ABSTRACT

The invention relates to an improved process of producing a fermentation product, such as ethanol, from starch-containing material using an increased dosage of alpha-amylase during liquefaction, which results in increased conversion of dextrins compared to conventional processes, and/or a reduced dosage of carbohydrate-generating enzyme during simultaneous saccharification and fermentation compared to a conventional process carried out at the same conditions. A process of the invention results in an increased yield. The invention also relates to an improved process of producing a fermentation product resulting in substantially the same yield as a conventional process, wherein reduced dosage of carbohydrate-source generating enzyme is used during simultaneous saccharification and fermentation.

21 Claims, 2 Drawing Sheets

U.S. PATENT DOCUMENTS

2004/0091983 A1 * 5/2004 Veit et al. .................. 435/161

FOREIGN PATENT DOCUMENTS

| | | |
|---|---|---|
| WO | WO 9919467 A1 * | 4/1999 |
| WO | WO 01/62947 | 8/2001 |
| WO | WO 02/38787 | 5/2002 |
| WO | WO 02/074895 | 9/2002 |
| WO | 2004/029193 A1 | 4/2004 |
| WO | 2004/106533 A1 | 12/2004 |
| WO | 2005/010193 A2 | 2/2005 |
| WO | 2006/086792 A1 | 8/2006 |

* cited by examiner

PROCESS OF PRODUCING A FERMENTATION PRODUCT

CROSS-REFERENCE TO RELATED APPLICATIONS

This application is a 35 U.S.C. 371 national application of PCT/US2006/036474 filed Sep. 19, 2006, which claims priority or the benefit under 35 U.S.C. 119 of U.S. provisional application no. 60/718,849 filed Sep. 20, 2005, the contents of which are fully incorporated herein by reference.

FIELD OF THE INVENTION

The present invention relates to a process for producing a fermentation product, such as ethanol, from starch-containing material.

BACKGROUND OF THE INVENTION

A vast number of commercial products that are difficult to produce synthetically may be produced by fermentation. Such products include alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yoghurt and cheese), leather, and tobacco industries.

The yield of fermentation processes have been increased significantly over the last decade.

CA 1,143,677 discloses a process of producing ethanol by fermenting in the presence of ferments of amylolytic or cellulolytic action.

U.S. Pat. No. 5,231,017 disclose a process of producing ethanol, wherein a protease is introduced during saccharification.

WO 01/62947 discloses a process of producing ethanol wherein a phytase is added during fermentation WO 02/38787 discloses a process of producing ethanol by fermentation, wherein secondary liquefaction is carried out in the presence of a thermostable acid alpha-amylase or a thermostable Maltogenic acid alpha-amylase.

WO 02/074895 discloses a process of producing a fermentation product, wherein fermentation is carried out in the presence of at least one carbohydrate-source generating enzyme and at least one alpha-amylase.

There is a need for further improvement of fermentation product processes, such as ethanol manufacturing processes.

SUMMARY OF THE INVENTION

In the first aspect the present invention relates to a process of producing a fermentation product from starch-containing material, which process comprises:
i) liquefying starch-containing material with alpha-amylase dosed in an amount from 0.05-2.6 KNU(S)/g dry solid starch-containing material,
ii) saccharifying the starch-containing material obtained in step i) with a carbohydrate-source generating enzyme performance dosage corresponding to from 0.20-1.00 AGU/g dry solid starch-containing material of *Talaromyces emersonii* glucoamylase, and
iii) fermenting in the presence of a fermenting organism.

Fermentation products, such as ethanol, may optionally be recovered after fermentation, preferably by distillation. Any enzymes having the above mentioned enzyme activities may be used according to the invention. Suitable enzymes are listed in the "Enzyme Activities"-section below. However, in a preferred embodiment the alpha-amylase, preferably bacterial alpha-amylase, used in step i) is derived from the genus *Bacillus*, especially a strain of *Bacillus stearothermophilus* or a variant thereof.

In a preferred embodiment the carbohydrate-source generating enzyme used in step ii) is a glucose-source generating enzyme and/or a maltose-generating enzyme.

In a preferred embodiment the fermenting organism used for fermentation in step iii) is yeast, preferably derived from a strain of *Saccharomyces*, preferably a strain of *Saccharomyces cerevisiae*.

DETAILED DESCRIPTION OF THE INVENTION

The present invention provides a process for producing a fermentation product, preferably an alcohol such as ethanol, from starch-containing material. A process of the invention includes a liquefaction step and sequentially or simultaneously performed saccharification and fermentation steps.

The inventors have found that an increased ethanol yield can be obtained by increasing the dosage of alpha-amylase used for liquefying starch-containing material (e.g., milled corn) compared to the dosage used in conventional processes, i.e., about 0.063 (KNU(S)/g DS corn). This is surprising considering the fact that alpha-amylase hydrolyses starch into dextrins that cannot directly be used as nutrient for a fermenting organisms such as yeast. The inventors also found that when using an increased dosage of alpha-amylase during liquefaction, resulting in a higher degree of conversion, i.e. higher DE, the dosage of carbohydrate-source generating enzyme during saccharification can be reduced compared to the dosage conventionally used, without causing a negative impact on ethanol yield. The higher degree of conversion (i.e., higher DE) results in higher ethanol yields. Further, it was found that a faster rate could be obtained by adding significantly higher amounts of alpha-amylase (0.67 KNU(S)/g DS corn—see Example 2) and the same or equivalent glucoamylase dosage. Further, the inventors also surprisingly found that significantly the same ethanol yield can be obtained if the conventionally used alpha-amylase dosage is used during liquefaction and the dosage of carbohydrate-source generating enzyme during saccharification is reduced. This is advantageous as the overall enzyme dosage can be reduced. Increase in conversion obtained by higher alpha-amylase dosage might be the reason for reduced need for enzyme that generates fermentable sugars. Example 1 illustrates the effect of increasing alpha-amylase dosage and/or simultaneously decreasing the carbohydrate-source generating enzyme dosage.

Raw Materials

The starch-containing starting material may according to the present invention be derived from any starch-containing plant material. Preferred starting materials may be selected from the group consisting of: tubers, roots, whole grain; and any combination thereof. In one embodiment, the starch-containing material is obtained from cereals. Suitable starch-containing cereals may be selected from the groups consisting of corn (maize), wheat, barley, cassava, sorghum, rye, and potato; and any combination thereof. Corn is the preferred raw material. In a process of the invention the starch-containing starting material is preferably whole grain or at least mainly whole grain. The starch-containing material may also consist of or comprise a side stream from starch processing, e.g., $C_6$ carbohydrate containing process streams that may not be suited for production of syrups.

Reducing the Particle Size of Starch-Containing Material

The starch-containing starting material may in a preferred embodiment be reduced in particle size prior to liquefaction. In a preferred embodiment the material is dry milled. The term "dry milling" denotes milling of the starch-containing material using, e.g., a hammer or roller mill. In the case of using whole grain milling the whole kernel is milled and used in a process of the invention. Similar particle size reducing technologies, such as emulsifying technology and rotary pulsation, are also contemplated according to the invention.

Process of the Invention

A process of the invention can generally be divided into the following main process stages: opening up the structure of the starch-containing material to allow further processing; liquefying the starch-containing material in order to hydrolyze (break down) starch to maltodextrins (dextrins); sequential or simultaneous saccharification and fermentation of the liquefied material to produce low molecular fermentable sugars that can be metabolized by a fermenting organism and converted into a desired fermentation product; and optionally recovery, by, e.g., distillation to purify the desired fermentation product.

The individual process steps of a process of the invention may be performed batch wise or continuously. Processes where all process steps are performed batch wise, or processes where all process steps are performed continuously, or processes where one or more process steps are performed batch wise and one or more process steps are performed continuously are equally contemplated according to the invention. The cascade process is an example of a process where one or more process steps are performed continuously and as such contemplated for the invention. For further information on the cascade process and other especially ethanol processes consult The Alcohol Textbook. Ethanol production by fermentation and distillation. Eds. T. P. Lyons, D. R. Kesall and J. E. Murtagh. Nottingham University Press 1995.

In the first aspect the present invention relates to a process of producing a fermentation product from starch-containing material, which process comprises:
i) liquefying starch-containing material with alpha-amylase dosed in an amount from 0.05-2.6 KNU(S)/g dry solid starch-containing material,
ii) saccharifying the starch-containing material obtained in step i) with a carbohydrate-source generating enzyme performance dosage corresponding to from 0.20-1.00 AGU/g dry solid starch-containing material of *Talaromyces emersonii* glucoamylase, and
iii) fermenting in the presence of a fermenting organism.

In a preferred embodiment the starch-containing material in step i) is liquefied with alpha-amylase dosed in an amount from 0.2-2.6 KNU(S)/g DS, preferably 0.5-2.6 KNU(S)/g DS, starch-containing material, followed by saccharifying the starch-containing material obtained in step i) with a carbohydrate-source generating enzyme performance dosage corresponding to from 0.20-0.50 AGU/g dry solid starch-containing material of *Talaromyces emersonii* glucoamylase.

The invention also relates to a process of producing a fermentation product from starch-containing material, which process comprises:
i) liquefying starch-containing material with alpha-amylase dosed in an amount from 0.070-0.50 KNU(S)/g dry solid starch-containing material,
ii) saccharifying the starch-containing material obtained in step i) with a carbohydrate-source generating enzyme performance dosage corresponding to from 0.20-1.00 AGU/g dry solid starch-containing material of *Talaromyces emersonii* glucoamylase, and
iii) fermenting in the presence of a fermenting organism.

In a preferred embodiment the

The "performance dosage" may differ from one carbohydrate-source generating enzyme, such as glucoamylase, to another.

The "performance dosage" is determined as AGU/g DS as described in the AGU assay in the "Material & Methods"-section below. The "performance dosage" that corresponds to that of *Talaromyces emersonii* glucoamylase (expressed recombinantly in an *Aspergillus niger* host cell as disclosed in WO 99/28448) can easily be determined by a person skilled in the art as follows:
1. Perform the experiment described in Example 1 using the carbohydrate-source generating enzyme in question,
2. From the carbohydrate-source generating enzyme dosage (in AGU/g DS) determined corresponding to an ethanol yield of, e.g., 11.74 a multiplication factor (MF) is calculated.
3. MF is used to calculate "performance dosage" in a dosage range within the scope of the present invention.

For instance, using *Aspergillus niger* glucoamylase as an example the "performance dosage" corresponding to 11.74 (% w/v) ethanol of *Talaromyces emersonii* glucoamylase (0.489 AGU/g DS) is 0.388. Thus, the multiplication factor (MF) is:

$$MF=0.388/0.489=0.793$$

The calculated "performance dosage" for *Aspergillus niger* glucoamylase (in AGU/g DS) is displayed in below table:

0.489 AGU (*Talaromyces*) corresponds to 0.489×0.793=0.388 AGU (*Aspergillus niger*)

| *Talaromyces emersonii* GA dose in AGU/g DS corn | *Aspergillus niger* GA Dose in AGU/g DS corn |
|---|---|
| 0.244 | 0.194 |
| 0.371 | 0.294 |
| 0.489 | 0.388 |

In an embodiment the starch-containing material in step i) is liquefied with alpha-amylase dosed in an amount from 0.080-0.40 KNU(S)/g dry solid starch-containing material, followed by saccharifying the starch-containing material obtained in step i) with a carbohydrate-generating enzyme performance dosage corresponding to from 0.20-0.50 AGU/g dry solid starch-containing material of *Talaromyces emersonii* glucoamylase.

In another embodiment the starch-containing material in step i) is liquefied with alpha-amylase dosed in an amount from 0.080-0.40 KNU(S)/g dry solid starch-containing material, followed by saccharifying the starch-containing material obtained in step i) using a carbohydrate-source generating enzyme performance dosage corresponding to from 0.20-0.40 AGU/g dry solid starch-containing material of *Talaromyces emersonii* glucoamylase.

In an embodiment the invention also relates to a process of producing a fermentation product from starch-containing material, which process comprises:

i) liquefying starch-containing material with alpha-amylase dosed in an amount from 0.050-0.50 KNU(S)/g dry solid starch-containing material, ii) saccharifying the starch-containing material obtained in step i) with a carbohydrate-source generating enzyme performance dosage corresponding to from 0.020-0.40 AGU/g dry solid starch-containing material of *Talaromyces emersonii* glucoamylase, and iii) fermenting in the presence of a fermenting organism In an embodiment the starch-containing material in step i) is liquefied with alpha-amylase dosed in an amount from 0.080-0.30 KNU(S)/g dry solid starch-containing material, followed by saccharifying the starch-containing material obtained in step i) with a carbohydrate-generating enzyme performance dosage corresponding to from 0.20-0.40 AGU/g dry solid starch-containing material of *Talaromyces emersonii* glucoamylase.

In another embodiment the starch-containing material in step i) is liquefied with alpha-amylase dosed in an amount from 0.050-0.80 KNU(S)/g dry solid starch-containing material, followed by saccharifying the starch-containing material obtained in step i) using a carbohydrate-source generating enzyme performance dosage corresponding to from 0.30-0.40 AGU/g dry solid starch-containing material of *Talaromyces emersonii* glucoamylase.

According to the invention the DE-value ("Dextrose Equivalent"-value) after step i) may be in the range from about 13-30, preferably about 14-25, more preferably 17-30, more preferably 18-30, more preferably 19-30, especially 20-30 determined using the Fehlings titration method described in the "Materials & Methods"-section below.

The DE value is a measure for reducing ends on $C_6$ carbohydrates. Pure dextrose (glucose) has a DE of 100. Dextrose is a reducing sugar. Whenever an alpha-amylase hydrolyzes a glucose-glucose bond in starch, two new glucose end-groups are exposed. At least one of these can act as a reducing sugar. Therefore the degree of hydrolysis can be measured as an increase in reducing sugars. The value obtained is compared to a standard curve based on pure glucose—hence the term dextrose equivalent. In other words: DE (dextrose equivalent) is defined as the amount of reducing carbohydrate (measured as dextrose-equivalents) in a sample expressed as w/w % of the total amount of dissolved dry matter.

Liquefaction

In step i) starch-containing material is broken down (hydrolyzed) into maltodextrins (dextrins). This step is referred to as "liquefaction". The starch-containing material as defined above in the "Raw Materials"-section may be reduced in particle size before liquefaction in step i). In a particular embodiment, the process of the invention further comprises, prior to the step i), the steps of:

x) reducing the particle size of starch-containing material;
y) forming a slurry comprising the starch-containing material and water and/or process water to obtain the starch material.

The aqueous slurry may contain from about 10-45 wt-% dry solid starch-containing material, preferably about 25-35 wt-% dry solid starch-containing material. In a preferred embodiment the starch-containing material is dry milled.

The slurry may include water and process waters, such as backset (thin stillage), scrubber water, evaporator condensate or distillate, side stripper water from distillation, or other fermentation product plant process water. Backset is the portion of liquid recycled to the front end operations, derived from the liquid phase (thin stillage) of a post-distillation centrifugation step. The other portion of this liquid phase is evaporated to become syrup and is sprayed onto the dried solid phase (whole stillage) to create the distillers dried grains with solubles (DDGS). The thin stillage (backset) is essentially a waste product in which roughly half of the total volume generated may be recycled as no environmentally friendly and/or commercially feasible means currently exist to dispose of this portion of the material. The acidic liquid (pH about 3.5-4.5) contains any soluble by-products derived from the entire fermentation product production process and includes some unconverted grain solids, usually at low concentrations of 5-7% dry substance (DS) along with other typical components such as sugars, salts, metals, proteins, organic acids and intracellular materials from lysed fermentation organism cells. In an embodiment an aqueous slurry containing between 0 to 70 vol.-% process water, preferably from about 15 to 60% vol.-% process water, especially from about 30 to 50 vol.-% process water, is used in liquefaction for preparing a slurry of starch-containing material.

According to one embodiment of the invention the slurry is heated to above the initial gelatinization temperature. The initial gelatinization temperature is dependent on the starch-containing material but can easily be determined by the skilled person in the art. In an embodiment the slurry is heated to a temperature between about 60-100° C., preferably between about 70-90° C. In an optional embodiment from 0-50%, preferably around 20-40%, of the total dosage of alpha-amylase added during liquefaction is added to the slurry in order to initiate thinning. The slurry of starch-containing material may in an optional embodiment be jet-cooked to gelatinize the starch-containing material at a temperature in the range from about 60-140° C., preferably between about 90-120° C., such as around 105° C., for 1-15 minutes, preferably for 3-10 minute, especially around 5 minutes, before being subjected to an alpha-amylase in step i) of the invention. According to the invention liquefaction step i) is carried out by treating the starch-containing material with an alpha-amylase at a temperature from around 60-100° C., preferably around 70-90° C. for 10-200 minutes, preferably 15-150 minutes. The alpha-amylase may be any alpha-amylase, including the ones mentioned in the "Alpha-Amylase"-section below. Preferred alpha-amylases are bacterial alpha-amylases, preferably derived from a strain of the genus *Bacillus*. Liquefaction may be performed at a pH in the range of about pH 4.0-7.0, preferably pH about 5.0-6.0. In an embodiment phytase is added during liquefaction.

Saccharification

In step ii) liquefied material, comprising maltodextrins, are hydrolyzed into low molecular fermentable sugars that can be metabolized by a suitable fermenting organism. This step is referred to as "saccharification". According to the present invention this step is carried out by subjecting the liquefied maltodextrin containing material to one or more carbohydrate-source generating enzymes, such as a glucose-source generating enzyme and/or a maltose-generating enzyme.

A saccharification step is typically carried out at a temperature in the range from about 30-70° C., such as around 60° C., at a pH in the range from 3.0 to 7.0, preferably 3.5 to 6.0, and may lasts for about 1-96 hours.

The saccharification and fermentation may in a preferred embodiment be combined to a simultaneous saccharification and fermentation process (SSF).

In an embodiment of the invention an optional pre-fermentation saccharification step of 1-6 hours may be included. Pre-fermentation saccharification may be carried out at any suitable process conditions known in the art. In an embodiment, the pre-saccharification is carried out at temperatures from 30-70° C., such as around 60° C., and at a pH in the range from 3.0 to 7.0, preferably 3.5 to 6.0. Thus, in one embodiment a process of the invention may include a pre-saccharification step, as described herein, which is performed after the liquefaction in step i) and before step ii) and/or iii).

When simultaneous saccharification and fermentation (SSF) is employed there is no significant holding stage for saccharification, meaning that a fermenting organism, such as yeast, and one or more carbohydrate-source generating enzymes are added essentially together. Steps ii) and iii) may be carried out simultaneously at a temperature between 28 and 38° C., preferably 29-37° C., especially 30-35° C., such as around 33° C. The pH during simultaneous saccharification and fermentation may be in the range between 3.0 and 7.0, preferably 3.5 and 6.0, and may typically last for 24-96 hours.

In an embodiment of the invention a pullulanase may be present during saccharification and/or fermentation. Any pullulanase may be used. Examples of contemplated pullulanases can be found in the "Pullulanases"-section below. Pullulanase may be added in an effective amount, including from between 1-100 micro g per g DS, especially from 10-60 micro g per g DS.

Fermentation

A fermentation step includes, without limitation, fermentation using a fermenting organism to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. Fermentation also include fermentations used in the consumable alcohol industry (e.g., beer and wine), dairy industry (e.g., fermented dairy products), leather industry and tobacco industry. Preferred fermentations include alcohol fermentation, as are well known in the art. Preferred fermentations are anaerobic fermentations, as are well known in the art.

The term "fermenting organism" refers to any organism suitable for use in a desired fermentation step iii) of the invention. Suitable fermenting organisms are according to the invention capable of fermenting, i.e., converting, preferably $DP_{1-3}$ sugars, such as especially glucose and maltose (i.e., carbohydrate source), directly or indirectly into the desired fermentation product, such as ethanol.

Examples of fermenting organisms include fungal organisms, such as yeast or filamentous fungi. Preferred yeast includes strains of the *Saccharomyces* spp., and in particular *Saccharomyces cerevisiae*. Commercially available yeast includes, e.g., ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIO-FERM AFT and XR (available from NABC—North American Bioproducts Corporation, GA, USA), GERT STRAND (available from Gert Strand AB, Sweden), and FERMIOL (available from DSM Specialties).

The fermentation is ongoing until the desired amount of fermentation product, such as ethanol, is produced. This typically means carrying out fermentation for 24-96 hours. The temperature and pH during fermentation is a temperature and pH suitable for the fermenting organism in question. For yeast, e.g., the temperature and pH is in the range about 28-38° C., preferably 29-37° C., especially 30-35° C., such as around 33° C., and the pH, e.g., is in the range about pH 3.0-7.0, e.g., about pH 3.5-6.0.

In an embodiment a protease and/or a phytase is added during fermentation.

Preferred yeast for ethanol production includes, e.g., *Pichia* and *Saccharomyces*. Preferred yeast according to the invention is *Saccharomyces* species, in particular *Saccharomyces cerevisiae* or bakers yeast.

Recovery

The process of the invention may optionally comprise recovering the fermentation product, such as ethanol; hence the fermentation product, e.g., ethanol, may be separated from the fermentation mash and purified. Following fermentation, the fermentation mash may be distilled to extract, e.g., ethanol or other liquid fermentation product. For instance, ethanol with a purity of above about 92 vol.-% ethanol can be obtained by the process of the invention.

Thus, in one embodiment, the fermentation in step iii) and a distillation step iv) may be carried out simultaneously and/or separately/sequentially; optionally followed by one or more process steps of further refinement.

Enzyme Activities

Alpha-Amylases

Step i) of the invention may be carried out using any suitable alpha-amylase. In a preferably embodiment a bacterial alpha-amylase may be used.

Bacterial Alpha-Amylases

Examples of suitable alpha-amylases include the below mentioned. Preferred bacterial alpha-amylases used in step i) may be derived from a strain of *Bacillus licheniformis*, *Bacillus amyloliquefaciens*, *Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO:3 disclosed in WO 99/19467.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Other contemplated bacterial alpha-amylases are KSM-K36 alpha-amylase disclosed in EP 1,022,334 and deposited as FERM BP 6945 and KSM-K38 alpha-amylase disclosed in EP 1,022,334, and deposited as FERM BP-6946. Also variants therefore are contemplated, in particular the variants disclosed in WO 02/31124 (from Novozymes A/S.

Commercially available bacterial alpha-amylase products and products containing alpha-amylases include TERMAMYL™ SC and LIQUOZYME™ SC, BAN (Novozymes A/S, Denmark) and DEX-LO™, SPEZYME™ ETHYL, SPEZYME™ AA, SPEZYME FRED-L, SPEZYME™ ALPHA, SPEZYME HPA and SPEZYME™ DELTA AA, SPEZYME™ XTRA, GC100 (from Genencor Int., USA), ULTRA-THIN (Valley Research, IN, USA.

Fungal Alpha-Amylases

Another maltose generating enzyme which may be used in a process of the invention is a fungal alpha-amylase (EC 3.2.1.1), preferably fungal acid alpha-amylases.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Fungal Hybrid Alpha-Amylases

In other contemplated embodiments the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or WO 2006/069290 or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in WO 2006/059290 or U.S. patent application No. 60/638,614 including Fungamyl variant with catalytic domain JA118 and *Athelia rolfsii* SBD (SEQ ID NO: 100 in WO 2006/069290 or U.S. 60/638,614), *Rhizomucor pusillus* alpha-amylase with *Athelia rolfsii* AMG linker and SBD (SEQ ID NO:101 in WO 2006/069290 or U.S. 60/638, 614), and *Meripilus giganteus* alpha-amylase with *Athelia rolfsii* glucoamylase linker and SBD (SEQ ID NO:102 in WO 2006/069290 or U.S. 60/638,614). Further contemplated is the hydrid *Rhizomucor pusillus* alpha-amylase with *Aspergillus niger* glucoamylase linker and SBD (which is disclosed in Table 5 as V039 as a combination of amino acid sequences SEQ ID NO:20 SEQ ID NO:72 and SEQ ID NO:96 in U.S. application Ser. No. 11/316,535 or WO 2006/069290). Other specifically contemplated hybrid alpha-amylases are any of the ones listed in Tables 3, 4, 5, and 6 in Example 4 in U.S. application Ser. No. 11/316,535 or WO 2006/0692890 (hereby incorporated by reference).

More specific examples of contemplated hybrid alpha-amylases are those disclosed in U.S. Patent Publication no. 2005/0054071, including those disclosed in Table 3 on page 15, such as *Aspergillus niger* alpha-amylase with *Aspergillus kawachii* linker and starch binding domain.

Commercial available compositions comprising fungal alpha-amylase include FUNGAMYL™ and the acid fungal alpha-amylase sold under the trade name SP288 (available from Novozymes A/S, Denmark).

Carbohydrate-Source Generating Enzymes

According to the invention one or more carbohydrate-source generating enzymes are used for saccharifying liquefied starch-containing material. The term "carbohydrate-source generating enzyme" includes glucoamylase (being glucose generators), beta-amylase and maltogenic amylase (being maltose generators). A carbohydrate-source generating enzyme is capable of providing energy to the fermenting organism(s) used in a process of the invention for producing the desired fermentation product. The generated carbohydrate may be converted directly or indirectly to the desired fermentation product. The carbohydrate-source generating enzyme may be mixtures of enzymes falling within the definition. Especially contemplated compositions are mixtures of at least glucoamylase and alpha-amylase, preferably acid alpha-amylase, especially fungal acid alpha-amylase (see "Fungal Alpha-Amylases"-section above). In a preferred embodiment the ratio between fungal acid alpha-amylase activity (AFAU) per glucoamylase activity (AGU) (AFAU per AGU) is at least 0.1, in particular at least 0.16, such as in the range from 0.12 to 0.50 or even higher.

Examples of contemplated glucoamylases, maltogenic amylases, beta-amylases and fungal alpha-amylase are set forth in the sections below.

Glucoamylase

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *A. niger* G1 or G2 glucoamylase (Boel et al. (1984), EMBO J. 3 (5), p. 1097-1102), or variants thereof, such as disclosed in WO 92/00381, WO 00/04136 add WO 01/04273 (from Novozymes, Denmark); the *A. awamori* glucoamylase (WO 84/02921), *A. oryzae* (Agric. Biol. Chem. (1991), 55 (4), p. 941-949), or variants or fragments thereof.

Other *Aspergillus* glucoamylase variants include variants to enhance the thermal stability: G137A and G139A (Chen et al. (1996), Prot. Eng. 9, 499-505); D257E and D293E/Q (Chen et al. (1995), Prot. Engng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Engng. 10, 1199-1204. Other glucoamylases include *Athelia rolfsii* (previously denoted *Corticium rolfsii*) glucoamylase (see U.S. Pat. No. 4,727,026 and (Nagasaka, Y. et al. (1998) Purification and properties of the raw-starch-degrading glucoamylases from *Corticium rolfsii*, Appl Microbiol Biotechnol 50:323-330), *Talaromyces* glucoamylases, in particular, derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215). Bacterial glucoamylases contemplated include glucoamylases from the genus *Clostridium*, in particular *C. thermoamylolyticum* (EP 135, 138), and *C. thermohydrosulfuricum* (WO 86/01831). The glucoamylase may also be from a strain of the genus *Trametes*, preferably derived from a strain of *Trametes cingulata* (as disclosed and defined in claim 1 of WO 2006/069289); or a strain of the genus *Pachykytospora*, preferably derived from a strain of *Pachykytospora papyracea* (as disclosed and defined in claim 2 in WO 2006/069289—hereby incorporated by reference). Also contemplated is the *Trichoderma reesei* glucoamylase disclosed as SEQ ID NO: 4 in WO 2006/060062 (hereby incorporated by reference) and further glucoamylases being at least 80%, preferably at least 90% identical thereto and further the glucoamylase derived from *Humicola grisea* disclosed as SEQ ID NO: 3 in U.S. Ser. No. 10/992,187 (hereby incorporated by reference) or sequences having at least 80%, preferably at least 90% identity thereto.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR, G-ZYME™ 480 Ethanol, FERMENZYME™ L400, FERMENZYME™ C, DISTILLASE™ L-400 and L-500 (from Genencor Int.).

Maltogenic Amylases

Maltogenic amylases (glucan 1,4-alpha-maltohydrolase) are able to hydrolyse amylose and amylopectin to maltose in the alpha-configuration. Furthermore, a maltogenic amylase is able to hydrolyse maltotriose as well as cyclodextrins. Specifically contemplated maltogenic amylases may be derived from *Bacillus* sp., preferably from *Bacillus stearothermophilus*, most preferably from *Bacillus stearothermophilus* C599 such as the one described in EP120.693. This particular maltogenic amylase has the amino acid sequence shown as amino acids 1-686 of SEQ ID NO: 1 in U.S. Pat. No. 6,162,628. A preferred maltogenic amylase has an amino acid sequence having at least 70% identity to amino acids 1-686 of SEQ ID NO:1 in U.S. Pat. No. 6,162,628, preferably at least 80%, at least 85%, at least 90%, at least 92%, at least 95%, at least 96%, at least 97%, at least 98%, or particularly at least 99% identity. Most preferred variants of the maltogenic amylase are disclosed in WO 99/43794 (which is hereby incorporated by reference).

Beta-Amylases

Another maltose generating enzyme to be used in the processes of the invention may be a beta-amylase (E.C 3.2.1.2). Beta-amylase is the name traditionally given to exo-acting maltogenic amylases, which catalyze the hydrolysis of 1,4-alpha-glucosidic linkages in amylose, amylopectin and related glucose polymers.

Beta-amylases have been isolated from various plants and micro-organisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7.0. Preferably the beta-amylase is derived from a filamentous fungus, such as a beta-amylase derived from *Rhizomucor pusilis*.

Contemplated beta-amylases include the beta-amylase from barley SPEZYME® BBA 1500, SPEZYME® DBA and OPTIMALT™ ME, OPTIMALT™ BBA from Genencor Int. as well as NOVOZYM™ WBA from Novozymes A/S.

Pullulanase

Pullulanases (E.C. 3.2.1.41, pullulan 6-glucano-hydrolase), are de-branching enzymes characterized by their ability to hydrolyze the alpha-1,6-glycosidic bonds in, for example, amylopectin and pullulan.

Specifically contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 and SEQ ID NO: 11 in U.S. Pat. No. 5,736,375 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

The pullulanase may according to the invention be added in an effective amount which include the preferred range of from between 1-100 micro g per g DS, especially from 10-60 micro g per g DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (Genencor Int., USA), and AMANO 8 (Amano, Japan).

Proteases

According to a process of the invention a protease may be present during fermentation or SSF. Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Suitable acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Especially contemplated are proteases derived from *Aspergillus niger* (see, e.g., Koaze et al., (1964), Agr. Biol. Chem. Japan, 28, 216), *Aspergillus saitoi* (see, e.g., Yoshida, (1954) J. Agr. Chem. Soc. Japan, 28, 66), *Aspergillus awamori* (Hayashida et al., (1977) Agric. Biol. Chem., 42(5), 927-933, *Aspergillus aculeatus* (WO 95/02044), or *Aspergillus oryzae*; and acidic proteases from *Mucor pusillus* or *Mucor miehei*.

Commercial proteases include GC 106 and SPEZYME FAN and FERMGEN™ (available from Genencor, USA). Suitable bacterial proteases, although not acidic proteases, include the commercially available products ALCALASE® and NEUTRASE® (available from Novozymes A/S).

Preferably, the protease is an aspartic acid protease, as described, for example, Handbook of Proteolytic Enzymes, Edited by A. J. Barrett, N. D. Rawlings and J. F. Woessner, Academic Press, San Diego, 1998, Chapter 270). Suitable examples of aspartic acid protease include, e.g., those disclosed in R. M. Berka et al. Gene, 96, 313 (1990)); (R. M. Berka et al. Gene, 125, 195-198 (1993)); and Gomi et al. Biosci. Biotech. Biochem. 57, 1095-1100 (1993), which are hereby incorporated by reference.

Protease may preferably be added in an amount of an amount of $10^{-7}$ to $10^{-5}$ gram active protease protein/g DS starch-containing material, in particular $10^{-7}$ to $5 \times 10^{-6}$ gram active protease protein/g DS starch containing material.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Enzymes:

Alpha-Amylase (M): *Bacillus stearothermophilus* alpha-amylase variant with the following mutations: I181*+G182*+N193F disclosed in U.S. Pat. No. 6,187,576 and available on request from Novozymes A/S, Denmark.

Glucoamylase (GA): *Talaromyces emersonii* glucoamylase disclosed as SEQ ID NO: 7 in WO 99/28448 with side activity of *Aspergillus niger* glucoamylase and *Aspergillus niger* acid alpha-amylase.

Other Materials

Yeast: ETHANOL RED™ yeast (available from Fermentis/Lesaffre, USA) LACTOSIDE™ available from Ethanol Technology, WI, USA Backset (or thin stillage): Acidic liquid (pH 3.5-4.5) containing soluble by-products derived from entire ethanol production process and includes some unconverted corn solids, such as low concentrations of 5-7% dry substance (DS) along with other components such as sugars, salts, metals, proteins, organic acids and intracellular materials from lysed yeast cells.

Determination of Identity

The degree of identity between two amino acid sequences are determined by the computer program GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for polypeptide sequence comparison are used: GAP creation penalty of 3.0 and GAP extension penalty of 0.1.

Determination of KNU(S) Using Konelab 30 Analyzer

BS-amylase in samples and the enzyme alpha-glucosidase in the reagent kit hydrolyze substrate (4,6-ethylidene($G_7$)-p-nitrophenyl($G_1$)-alpha-D-maltoheptaoside (ethylidene-$G_7$PNP)) to glucose and the yellow-colored p-nitrophenol.

The rate of formation of p-nitrophenol can be observed by Konelab 30. This is an expression of the reaction rate and thereby the enzyme activity.

Reaction Conditions
Reaction:
pH: 7.15
Temperature: 37° C.
Reaction Time: 180 sec
Detection
Wavelength: 405 nm
Measuring Time: 120 sec
Unit Definition

*Bacillus stearothermophilus* amylase (BS-amylase) activity is measured in KNU(S), Kilo Novo Units (*sterarothermophilus*), relative to an enzyme standard of a declared strength.

This analytical method is described in more details in EB-SM-0221.02 available from Novozymes A/S, Denmark, on request.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0309.02/01) describing this analytical method in more detail is available on request from Novozymes A/S, Denmark, which folder is hereby included by reference.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| Substrate | Soluble starch |
| --- | --- |
| Temperature | 37° C. |
| pH | 4.7 |
| Reaction time | 7-20 minutes |

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, glucoamylase wildtype *Aspergillus niger* G1, also disclosed in Boel et al. (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

Standard Conditions/Reaction Conditions: (Per Minute)

| Substrate: | Starch, approx. 0.17 g/L |
|---|---|
| Buffer: | Citate, approx. 0.03 M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, and incorporated by reference.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 ml diluted sample or standard is incubated at 40° C. for 2 minutes. 0.5 ml 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Determination of Dextrose Equivalent (DE) (Fehlings Titration Method):

Dextrose Equivalent (DE) is a measure of the degree of hydrolysis of starch (specifically whole grain corn). The Fehlings titration test, used to measure this, is based on the reduction of cupric ion to cuprous ion by the presence of reducing sugars. Excess cupric ion then reduces the iodide ion in an acidic media, forming the tri-iodide ion. The tri-iodide ion is then titrated with a standardized Sodium thiosulfate solution. The titer of an unknown sample is then compared to one obtained by titration against a 1.0% w/v glucose solution and one with only distilled or reverse osmosis water present (zero reducing sugars) to calculate a relative value.

EXAMPLES

Example 1

Ethanol Yields from Modified Amylase Dosing Combinations

To investigate the effect of various alpha-amylase and glucoamylase dosing combinations, liquefaction and simultaneous saccharification and fermentation (SSF) experiments were performed using the following experimental design:

TABLE 1

Experimental design for liquefaction and SSF
n = 9 for each treatment (81 total fermentations).

| Liq. Treatment | AA Dose (KNU(S)/g DS corn | Liq. Mash Temp. (° C.) | Liq. Time (minutes) | SSF Treatment | GA Dose (AGU/g DS corn | SSF Temp. (° C.) | SSF Time (hrs) |
|---|---|---|---|---|---|---|---|
| Liq 1 DE = 15.0 | 0.063 | 85 | 90 | SSF 1 SSF 2 SSF 3 | 0.244 0.371 0.489 | 33 | 72 |
| Liq 2 DE = 16.3 | 0.094 | 85 | 90 | SSF 1 SSF 2 SSF 3 | 0.244 0.371 0.489 | 33 | 72 |
| Liq 3 DE = 17.4 | 0.126 | 85 | 90 | SSF 1 SSF 2 SSF 3 | 0.244 0.371 0.489 | 33 | 72 |

A 32 wt.-% DS (dry substance) slurry was created from dry milled corn flour, process backset and tap water. The pH was adjusted to 5.89 using 5N NaOH and 1N HCl. The slurry was distributed in equal amounts to three 2 L liquefaction vessels and dosed with respective amounts of alpha-amylase (AA). The vessels were placed in a water bath set at 86° C. (corresponding to a mash temperature of 85° C.). Liquefaction of each treatment was carried out for 90 minutes with agitation. Once complete, each vessel was immediately placed in an ice water bath and allowed to cool to room temperature. 2 ppm LACTOSIDE™ (antibiotic) and 1,000 ppm urea were added to each vessel and mixed thoroughly. The dry substance level was adjusted to 30.9% DS by adding tap water, and final DE values were obtained using above mentioned Fehlings titration method (see Table 1 for values).

The liquefact was then transferred to 50 ml polystyrene tubes for the SSF phase, targeting approximately 14 g mash/tube. The screw caps were punctured with a 21 gauge needle to allow $CO_2$ escape. For each liquefaction treatment (n=3), three dose levels of glucoamylase (GA) were evaluated (0.244, 0.371, and 0.489 AGU/g dry solid (DS) corn. Re-hydrated ETHANOL RED™ yeast was dosed into each tube, targeting $3.0 \times 10^7$ viable cells/ml of mash. Tubes were vortexed, weighed, and placed in the 33° C. water bath. Fermentation progress was monitored by periodically weighing the tubes and recording $CO_2$ weight loss. Tubes were vortexed briefly before each weighing. From the $CO_2$ weight loss readings, ethanol yield (g ethanol/g DS) was calculated using the following formula: (data not shown)

$$\text{g ethanol/g DS} = \frac{\text{g } CO_2 \text{ weight loss} \times \frac{1 \text{ mol } CO_2}{44.0098 \text{ g } CO_2} \times \frac{1 \text{ mol ethanol}}{1 \text{ mol } CO_2} \times \frac{46.094 \text{ g ethanol}}{1 \text{ mol ethanol}}}{\text{g corn mash} \times \%\text{DS corn}}$$

In Table 2, the information in italics corresponds to the conventional alpha-amylase dose combination (benchmark), the information in bold indicates all dosing combinations resulting in statistically higher final ethanol concentrations than benchmark ($\alpha=0.05$), and the information in bold italics indicates combinations resulting in ethanol concentrations statistically equivalent to benchmark ($\alpha=0.05$).

TABLE 2

72-hour HPLC analysis for final ethanol concentration.
n = 3 for each treatment.

| | AA Dose (KNU(S)/g DS corn) | GA Dose (AGU/g DS corn) | Ethanol (% w/v) |
|---|---|---|---|
| Higher Ethanol | 0.126 | 0.489 | 12.21 |
| | 0.126 | 0.371 | 12.09 |
| | 0.126 | 0.244 | 11.97 |
| | 0.094 | 0.489 | 11.90 |
| Conventional Dose | *0.094* | *0.371* | *11.80* |
| | 0.063 | 0.489 | 11.74 |
| | *0.094* | *0.244* | *11.73* |
| | *0.063* | *0.371* | *11.64* |
| | 0.063 | 0.244 | 11.59 |

The data illustrates advantages of increasing AA dose alone and/or simultaneously decreasing GA dose. The most significant benefit is observed at the highest AA dose (0.126 KNU(S)/g DS corn) for which there appears to be a considerable range of GA doses that produce higher ethanol concentrations than the conventional combination. Alternatively, obtaining equivalent ethanol levels may be possible by simply reducing GA dose or by slightly increasing AA dose while simultaneously decreasing GA dose.

Example 2

Increased Fermentation Kinetics

To investigate the effect of various alpha-amylase and glucoamylase dosing combinations on fermentation rate, liquefaction and simultaneous saccharification and fermentation (SSF) experiments were performed using the following experimental design:

TABLE 3

Experimental design for liquefaction and SSF
n = 9 for each treatment

| Liq. Treatment | AA Dose (KNU(S)/g DS corn) | Liq. Mash Temp. (° C.) | Liq. Time (minutes) | GA Dose (AGU/g DS corn) | SSF Temp. (° C.) | SSF Time (hrs) |
|---|---|---|---|---|---|---|
| Liq 1 DE = 14.5 | 0.047 | 85 | 90 | 0.489 | 33 | 72 |
| Liq 2 DE = 17.5 | 0.094 | 85 | 90 | 0.489 | 33 | 72 |

A 33 wt.-% DS (dry substance) slurry was created from dry milled corn flour, process backset, and tap water. The pH was adjusted to about 5.8 using 5N NaOH and 1N HCl. The slurry was distributed in equal amounts into 2 L liquefaction vessels and dosed with respective amounts of alpha-amylase (AA). The vessels were placed in a water bath set at 86° C. (corresponding to a mash temperature of 85° C.). Liquefaction of each treatment was carried out for 90 minutes with agitation. Once complete, each vessel was immediately placed in an ice water bath and allowed to cool to room temperature. 2 ppm LACTOSIDE™ (antibiotic) and 1,000 ppm urea were added to each vessel and mixed thoroughly. The dry substance level going into fermentation was 35.2% DS, and final DE values were obtained using above mentioned Fehlings titration method (see table 2 for DE values).

The liquefact was then transferred to 50 ml polystyrene tubes for the SSF phase, targeting approximately 14 g mash/tube. The screw caps were punctured with a 21 gauge needle to allow $CO_2$ escape. The needles were left in the caps for the entire SSF process. For each liquefaction treatment, GA was dosed at 0.489 AGU/g dry solid (DS) corn. Re-hydrated ETHANOL RED™ yeast was dosed into each tube, targeting $3.0 \times 10^7$ viable cells/ml of mash. Tubes were vortexed, weighed, and placed in the 33° C. water bath. Fermentation progress was monitored by periodically weighing the tubes and recording $CO_2$ weight loss. Tubes were vortexed briefly before each weighing. From the $CO_2$ weight loss readings, ethanol yield (g ethanol/g DS) was calculated using the following formula: (data not shown)

$$\text{g ethanol/g DS} = \frac{\text{g } CO_2 \text{ weight loss} \times \frac{1 \text{ mol } CO_2}{44.0098 \text{ g } CO_2} \times \frac{1 \text{ mol ethanol}}{1 \text{ mol } CO_2} \times \frac{46.094 \text{ g ethanol}}{1 \text{ mol ethanol}}}{\text{g corn mash} \times \%\text{DS corn}}$$

Figure 1:
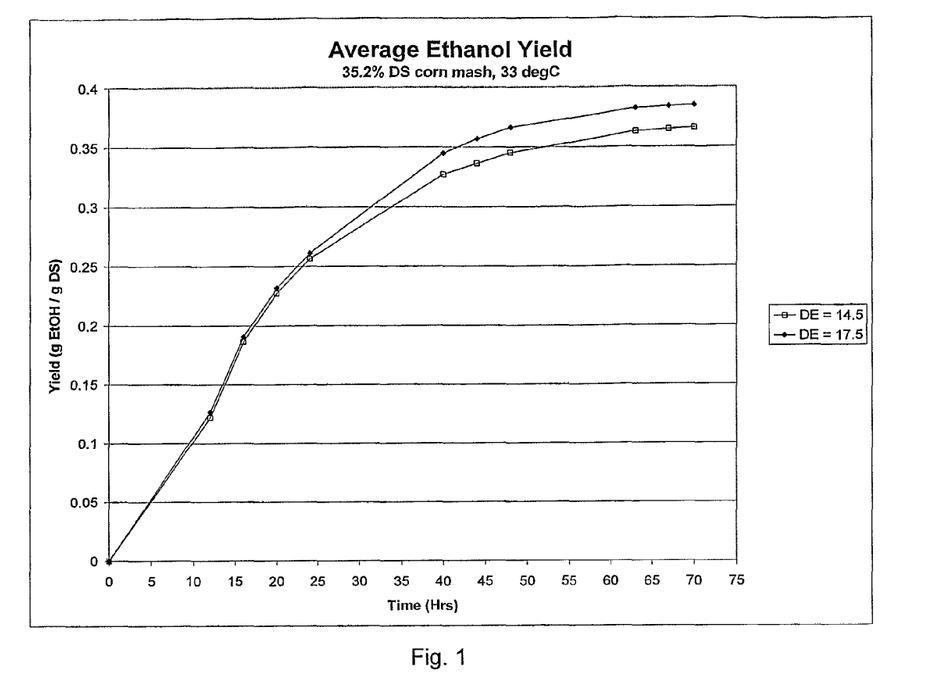
FIG. 1 shows the fermentation kinetics during fermentation.

In FIG. 1 the fermentation kinetics during fermentation is displayed. It can be seen that fermentation kinetics is slightly faster during the first 24 hours of fermentation. After 24 hours, fermentation rate increases significantly for high DE mash (17.5) and results in 5.2% higher ethanol yield on average verses lower DE mash (14.5).

Example 3

DE at High Alpha-Amylase Dosage

This experiment was carried out to investigate the Dextrose Equivalent (DE) effect at a high alpha-amylase dosage.

A 32 wt.-% DS (dry substance) slurry was created from dry milled corn flour, process backset and tap water, as in Example 1. The pH was adjusted to about 5.7 using 5N NaOH and 1N HCl. The slurry was added to a 2 L liquefaction vessel and placed in a water bath. 0.062 KNU(S)/g DS alpha-amylase (AA) was added. The mash temperature was determined to be 84° C. Liquefaction was initially carried out for 150 minutes with agitation. After 150 minutes 2.50 KNU(S)/g DS was added and liquefaction was continued for another 180 minutes (i.e., total of 330 minutes). During liquefaction the DE was determined using "Fehling's titration method" described in the "Materials & Methods" section.

Figure 2:
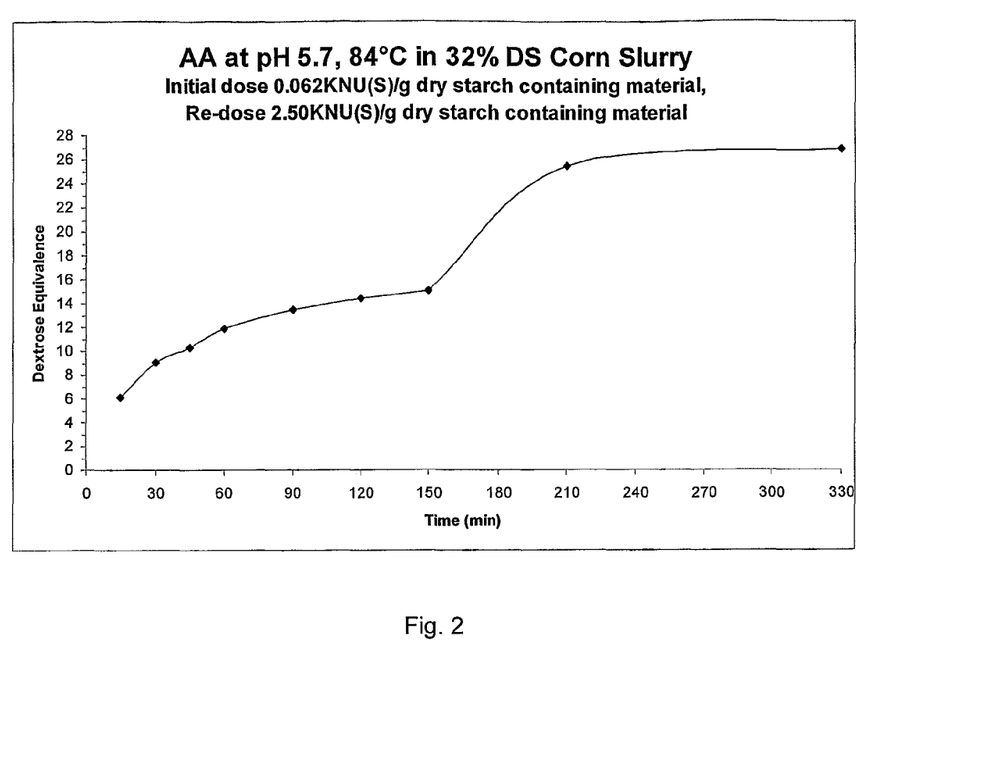
FIG. 2 shows the effect on DE when adding high alpha-amylase dosage.

As can be seen from FIG. 2 the experiment showed that the DE was about 15 after the initial 150 minutes. After re-dosing alpha-amylase the DE increased and reached a DE value around 28 after 330 minutes.

The invention claimed is:

1. A process of producing a fermentation product, comprising:
   (a) liquefying a starch-containing material with an alpha-amylase at a dose of 0.08-2.6 KNU(stearothermophilus)/g dry solid starch-containing material,
   (b) saccharifying the starch-containing material obtained in step (a) with a carbohydrate-source generating enzyme at a dose corresponding to 0.20-1.00 AGU of *Talaromyces emersonii* glucoamylase/g dry solid starch-containing material, and
   (c) fermenting the liquefied and/or saccharified starch containing material in the presence of a fermenting organism.

2. The process of claim 1, wherein the dose of the alpha-amylase is 0.08-0.50 KNU(stearothermophilus)/g dry solid starch-containing material.

3. The process of claim 1, wherein the dose of the alpha-amylase is 0.08-0.40 KNU(stearothermophilus)/g dry solid starch-containing material.

4. The process of claim 1, wherein the dose of the alpha-amylase is 0.08-0.30 KNU(stearothermophilus)/g dry solid starch-containing material.

5. The process of claim 1, wherein the alpha-amylase is a *Bacillus stearothermophilus* alpha-amylase or a variant thereof in which I181 and G182 are deleted.

6. The process of claim 1, wherein the carbohydrate-source generating enzyme is selected from the group consisting of glucose-generating enzymes and maltose-generating enzymes.

7. The process of claim 6, wherein the carbohydrate-source generating enzyme is a glucoamylase.

8. The process of claim 7, wherein the carbohydrate-source generating enzyme is *Talaromyces emersonii* glucoamylase.

9. The process of claim 6, wherein the carbohydrate-source generating enzyme is a maltogenic amylase or a beta-amylase.

10. The process of claim 1, wherein the dose of the carbohydrate-source generating enzyme corresponds to 0.20-0.50 AGU *Talaromyces emersonii* glucoamylase/g dry solid starch-containing material.

11. The process of claim 1, wherein the dose of the carbohydrate-source generating enzyme corresponds to 0.20-0.40 AGU *Talaromyces emersonii* glucoamylase/g dry solid starch-containing material.

12. The process of claim 1, wherein the dose of the carbohydrate-source generating enzyme corresponds to 0.30-0.40 AGU *Talaromyces emersonii* glucoamylase/g dry solid starch-containing material.

13. The process of claim 1, wherein the fermentation product is ethanol.

14. The process of claim 1, wherein the starch-containing material is liquefied to a dextrose equivalent of 13-30.

15. The process of claim 1, further comprising recovering the fermentation product after fermentation.

16. The process of claim 1, further comprising prior to step (a) the steps of:
   x) reducing of particle size of starch-containing material; and
   y) forming a slurry comprising the startch containing material and water.

17. The process of claim 16, wherein the particle size of the starch-containing material is reduced by milling.

18. The process of claim 17, wherein the starch-containing material is dry milled.

19. The process of claim 1, wherein the alpha-amylase is a *Bacillus* alpha-amylase.

20. The process of claim 1, wherein the saccharification and the fermentation are carried out simultaneously.

21. The process of claim 1, wherein the starch-containing material is selected from the group consisting of tubers, roots, whole grain, and any combination thereof.

* * * * *